United States Patent [19]

Toyama et al.

[11] 4,217,131
[45] Aug. 12, 1980

[54] HERBICIDAL COMPOSITION

[75] Inventors: Teruhiko Toyama, Fujisawa; Osamu Morikawa, Chigasaki; Toshimi Tanaka, Chigasaki; Yoshikata Hojo, Chigasaki; Yoshio Takasawa, Chigasaki; Taisuke Kurechi, Yokohama, all of Japan

[73] Assignee: Mitsui Toatsu Chemicals, Incorporated, Tokyo, Japan

[21] Appl. No.: 613,034

[22] Filed: Sep. 12, 1975

[30] Foreign Application Priority Data

Sep. 24, 1974 [JP] Japan ................... 49-108856

[51] Int. Cl.² .............................................. A01N 9/20
[52] U.S. Cl. .......................... 71/108; 71/116; 71/118
[58] Field of Search .......................... 71/118, 116, 108

[56] References Cited

U.S. PATENT DOCUMENTS

| | | | |
|---|---|---|---|
| 2,396,513 | 3/1946 | Jones | 71/116 |
| 3,547,620 | 12/1970 | Olin | 71/118 |
| 3,663,200 | 5/1972 | Olin | 71/118 |

FOREIGN PATENT DOCUMENTS

| | | | |
|---|---|---|---|
| 72638 | 4/1970 | German Democratic Rep. | |
| 43-16465 | 11/1968 | Japan | 71/116 |
| 46-14077 | 4/1971 | Japan | 71/118 |

OTHER PUBLICATIONS

De Datta et al., "Selectivity of Some New Herbicides for Direct–Seeded Flooded Rice in the Tropics", *Weed Reg.*, 1971, 11(1), 41–46.
Baer et al., Chem. Abst., vol. 74 (1971), 2940b.
DeDatta et al., Chem. Abst., vol. 75, (1971), 108798d.

*Primary Examiner*—Catherine L. Mills
*Attorney, Agent, or Firm*—Fisher, Christen & Sabol

[57] ABSTRACT

Employment of N-(butoxymethyl)-2-chloro-2',6'-diethyl acetanilide in combination with at least one α-(β-naphthoxy)-propionic acid derivative as active ingredients provides an excellent herbicidal composition effective on a variety of weeds.

13 Claims, No Drawings

HERBICIDAL COMPOSITION

BACKGROUND OF THE INVENTION

Many effective components have been proposed hitherto for a herbicidal composition. Most of the components, however, give a high herbicidal effect on a certain kind of weed but have almost no effect on another. For this reason, when controlling plant growth, it is necessary to apply several herbicides in order to kill a variety of weeds. Accordingly, a total amount of the effective components increases, causing damaged to the plant. Moreover, in recent years, the problem of environmental pollution has been raised in connection with the use of agricultural chemicals. The use of a highly effective herbicidal composition in an amount as small as possible is recommended to minimize any environmental effect. Under these circumstances, there is a great demand for a new type of a herbicidal composition which meets the aforementioned requirements.

SUMMARY OF THE INVENTION

This invention relates to a new herbicidal composition.

More particularly, this invention relates to a new herbicidal composition containing as effective components at least one α-(β-naphthoxy)propionic acid derivative expressed by the following general formula (I)

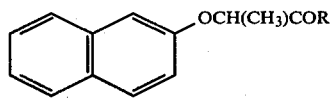 (I)

wherein R represents OH, OCH₃,

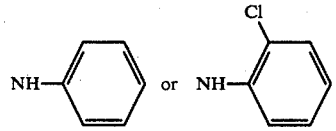

and N-(butoxymethyl)-2-chloro-2',6'-diethyl acetanilide (hereafter referred to as BCDA).

By the employment of the herbicidal composition of the present invention it is possible to control various kinds of weeds not only in paddy fields but also in upland fields.

The present invention also provides a herbicidal composition which exhibits excellent herbicidal effect even used in a smaller amount.

Thus, an object of the present invention is to provide a herbicidal composition which is effective on various kinds of weeds.

Another object of the present invention is to provide an easy method for controlling growth of plants by the use of small amounts of the herbicidal composition.

Other objects, features and merits of this invention will become apparent from the following detailed descriptions.

DETAILED DESCRIPTION OF THE INVENTION

An α-(β-naphthoxy)propionic acid derivative which is one of the effective components of the herbicidal composition of the invention and which is expressed by the general formula (1) gives a high herbicidal effect on broad-leaved weeds and certain kinds of weeds of cyperaceae but has almost no effect on weeds of gramineae. While, BCDA, which is the other effective component of the herbicidal composition of the invention, has a great weed-killing effect on weeds of gramineae but is rather ineffective against broad-leaved weeds and weeds of cyperaceae. These herbicidal tendencies become more clear in a rice field where weeds reach their almost full growth.

However, the herbicidal composition of the invention which contains as it main components the compound of the general formula (1) and BCDA in a suitable mixing ratio shows an unexpectedly pronounced herbicidal effect, on perennial weeds such as sagittaria pygmaea, scirpus hotarui alisma canalicutatum a. br. et bouche, sagittaria trifolia, cyperus serotinus rottb and eleocharis kuroguwai ohwi as well as annual weeds even when used in such a small amount as would not be expected to kill the weeds by application of each of the effective components. In addition, the composition gives no ill effect on a waterfield rice plant. Furthermore, the composition of the invention may also be employed as a herbicidal agent for farm weeds and serves to completely control farm weeds, which are hard to kill by the respective components, without increasing a total amount of the respective components. The composition does not give any ill chemical effect on farm products as well.

Examples of the compound of the general formula (1) useful in the present invention are as follows:

| Compound symbol | Chemical structure | Melting point (or boiling point) |
|---|---|---|
| Compound A | ⬡⬡–OCH(CH₃)COOCH₃ | 57.5°–58.5° C. |
| Compound B | ⬡⬡–OCH(CH₃)CONH–⬡ | 127.0°–128.0° C. |

| Compound symbol | Chemical structure | Melting point (or boiling point) |
|---|---|---|
| Compound C | [naphthalene]–OCH(CH₃)CONH–[2-chlorophenyl] | greater than 220° C. under 5 mmHg |
| Compound D | [naphthalene]–OCH(CH₃)COOH | 107.5°–109.0° C. |

A process for preparing the compound of the general formula (I) is disclosed in Japanese Patent Publication No. 46 - 14077. A process of the preparation of BCDA is disclosed in Japanese Patent Publication No. 48 - 37820.

The amounts of the compound of the aforementioned general formula (1) and of BCDA which constitute the main effective components of the herbicidal composition of the invention can be reduced to a greater extent than in case where these compounds or agents are used singly. A mixing ratio of these compounds is most preferable to be 0.3–1 part by weight of BCDA per part by weight of the compound expressed by the general formula (1).

The composition of the invention is generally employed in the form of granular, wettable powder or dust, and may be diluted with water and applied to a rice or farm field or may be directly applied in the above-mentioned form. Further, an insecticide, a fungicide or other herbicides may be mixed with the composition of the invention. These mixtures may also be formed into a suitable shape for specific end use, if necessary.

The concentration of the effective components of the herbicidal composition of the present invention varies with the type of the composition and is preferably 10–20% in the case of granular, 60–70% in the case of wettable powder and 10–15% in the case of dust.

A total amount of the effective components applied to the fields is 10–40 g/are, preferably 25–35 g/are.

The present invention will be particularly illustrated in the following examples, which should not be construed as limiting the invention. In the Examples, parts are by weight.

EXAMPLE 1

Granular 10 parts of compound A, 5 parts of BCDA, 60 parts of bentonite, 21 parts of talc, 1 part of sodium dodecylbenzenesulfonate, 1 part of polyoxyethylene alkylallyl ether, and 2 parts of sodium lignosulfonate were mixed with each other, to which was added a predetermined amount of water for kneading. Then, the mixture was subjected to granulation by a usual method using a granulating machine to obtain 100 parts of granules.

EXAMPLE 2

Granular 7 parts of compound B, 7 parts of BCDA, 53 parts of bentonite, 30 parts of talc, 2 parts of a naphthalenesulfonic acid mixture, and 1 part of dioctylsulfosuccinate were mixed with each other, to which was added a predetermined amount of water for kneading. The mixture was subjected to granulation by a usual method using a granulating machine to obtain 100 parts of granules.

EXAMPLE 3

Granular 8 part of compound C, 32 parts of bentonite, 52 parts of talc, 2 parts of sodium lignosulfonate, and 1 part of sodium dodecylbenzenesulfonate were mixed with each other, to which was added a predetermined amount of water, followed by granulation by a usual method using a granulating machine. The resultant granules were dried and impregnated with 5 parts of BCDA to obtain 100 parts of a granular agent.

EXAMPLE 4

Granular 7 parts of compound B, 4 parts of BCDA, 60 parts of bentonite, 26 parts of clay, 2.5 parts of sodium alkylbenzenesulfonate, and 0.5 parts of polyvinyl alcohol were uniformly mixed with each other, to which was added a predetermined amount of water for kneading, followed by granulation by a usual method using a granulating machine to obtain 100 parts of granules.

EXAMPLE 5

Dust 9 parts of compound B, 4 parts of BCDA and 87 parts of diatomaceous earth and clay were mixed and finely powdered to obtain 100 parts of a powdery agent.

EXAMPLE 6

Wettable powder 30 parts of compound A, 15 parts of BCDA, 10 parts of white carbon, 40 parts of diatomaceous earth, 3 parts of sodium lignosulfonate, and 2 parts of sodium dodecylbenzenesulfonate were mixed with each other under grinding conditions to obtain 100 parts of a hydrate agent.

EXAMPLE 7

Granular 10 parts of compound D, 5 parts of BCDA, 52 parts of bentonite, 30 parts of talc, 2 parts of a naphthalenesulfonic acid mixture, 1 part of dioctylsuccinate were mixed with each other, to which was added a predetermined amount of water for kneading. The mixtutre was subjected to granulation by a usual method using a granulating machine to obtain 100 parts of a granular agent.

EXAMPLE 8

Wettable powder 30 parts of compound D, 15 parts of BCDA, 10 parts of white carbon, 40 parts of diatomaceous earth, 3 parts of a naphthalenesulfonic acid mixture, and 2 parts of dioctylsuccinate were mixed with each other under grinding conditions to obtain 100 parts of a hydrate agent.

The herbicidal effects of the composition of the present invention will be particularly illustrated in the following experimental examples.

TEST EXAMPLE 1

Herbicidal test in an initial stage of germination in paddy field 11 kg of a rice field soil was placed in a 1/2,000 are Wagener's pot and uniformly manured with a chemical fertilizer having N, $P_2O_5$ and $K_2O$ components each in an amount of 1 g. To the soil was added a suitable amount of water with sufficient kneading, followed by further adding water thereto to such an extent as to be full to overflowing. Then, two rice stubbles each composed of two young rice plants (with a p. 10 leaf stage of 2.5) which had been previously grown in a greenhouse were planted to the pot in a depth of 3 cm. To the pot were sowed seeds of echinochloa crus-galli, cyperus difformis, monochoria vaginalis press, scirpus hotarui, and alisma canaliculatum a. br. et bouche. Further, three kinds of tubers Sagittaria pygmaea miq. cyperus serotinus rottb, and eleocharis kuroguwai ohwi, and a hibernated germ of eleocharis acicularis were transplanted and grown in the greenhouse while maintaining the water depth of 3 cm.

3 days after the plantation, i.e., in an early stage of germination of the weeds, a predetermined amount of the composition was applied to the test pot in the form of granules which were prepared in almost the same method as in the foregoing examples. After the application, water in the pot was allowed to leak at a rate of 1 cm/day.

One month after the treatment, a residual amount of the weeds and the ill effect of the composition on rice plants were checked.

The tests were repeated using each component compounds or compositions of the invention, and commercially available herbicidal agents.

The results of these tests are shown in Table 1 below.

Table 1

| Tested Compound or composition | Amount (g/a) | Residual Amount of Weeds (air dried weight g/pot) | | | | | | | | | Chemical Damage on Rice plant |
|---|---|---|---|---|---|---|---|---|---|---|---|
| | | Annual Weeds | | | Perennial Weeds | | | | | | |
| | | Echinochloa crusgalli | Cyperus difformis | Monochoria vaginalis presl | Scirpus hotarui | Eleocharis acicularis | Alisma canaliculatum a. br. et bouche | Sagittaria pygmaea miq. | Cyperus serotinus rottb | eleocharis kuroguwai ohwi | |
| Compound A | 5 | 5.62 | 1.27 | 0.27 | 1.07 | 1.01 | 1.04 | 1.25 | 2.57 | 1.02 | nil |
| | 10 | 5.07 | 0.67 | 0.14 | 0.92 | 0.57 | 0.54 | 0.67 | 1.94 | 0.17 | " |
| | 20 | 5.01 | 0.09 | 0.09 | 0.08 | 0.12 | 0.09 | 0.27 | 0.99 | 0.09 | " |
| Compound B | 5 | 5.68 | 0.78 | 0.14 | 0.94 | 1.00 | 1.01 | 1.11 | 2.07 | 1.01 | nil |
| | 10 | 5.29 | 0.45 | 0.10 | 0.49 | 0.41 | 0.27 | 0.49 | 1.81 | 0.27 | " |
| | 20 | 5.14 | 0.07 | 0.08 | 0.02 | 0.09 | 0.02 | 0.09 | 0.87 | 0.05 | " |
| Compound C | 5 | 5.69 | 0.94 | 0.25 | 0.92 | 0.97 | 0.94 | 1.21 | 2.14 | 0.97 | nil |
| | 10 | 5.37 | 0.54 | 0.12 | 0.69 | 0.46 | 0.41 | 0.51 | 1.87 | 0.34 | " |
| | 20 | 5.29 | 0.09 | 0.08 | 0.07 | 0.10 | 0.04 | 0.12 | 0.92 | 0.08 | " |
| Compound D | 5 | 5.67 | 0.85 | 0.26 | 1.00 | 1.02 | 1.02 | 1.10 | 2.10 | 1.01 | nil |
| | 10 | 5.35 | 0.50 | 0.13 | 0.75 | 0.46 | 0.35 | 0.48 | 1.80 | 0.20 | " |
| | 20 | 5.25 | 0.09 | 0.08 | 0.08 | 0.09 | 0.02 | 0.10 | 0.97 | 0.09 | " |
| BCDA | 5 | 2.41 | 0.74 | 0.10 | 0.94 | 0.97 | 1.07 | 1.94 | 1.47 | 1.07 | very slightly |
| | 10 | 0.54 | 0.09 | 0.09 | 0.72 | 0.09 | 0.97 | 1.07 | 0.97 | 0.94 | to a slight degree |
| | 15 | 0.01 | 0.04 | 0.06 | 0.03 | 0.05 | 0.64 | 1.00 | 0.64 | 0.52 | to a modulate degree |
| Compound A + BCDA | 5 + 5 | 0.04 | 0 | 0.01 | 0.02 | 0 | 0.01 | 0.02 | 0.03 | 0.02 | nil |
| | 5 + 10 | 0 | 0 | 0 | 0 | 0 | 0 | 0 | 0 | 0 | " |
| | 10 + 5 | 0.06 | 0 | 0 | 0 | 0 | 0 | 0 | 0 | 0 | " |
| | 10 + 10 | 0 | 0 | 0 | 0 | 0 | 0 | 0 | 0 | 0 | " |
| Compound B + BCDA | 5 + 5 | 0.02 | 0 | 0.01 | 0.01 | 0 | 0.02 | 0.01 | 0.02 | 0.01 | nil |
| | 5 + 10 | 0 | 0 | 0 | 0 | 0 | 0 | 0 | 0 | 0 | " |
| | 10 + 5 | 0.04 | 0 | 0 | 0 | 0 | 0 | 0 | 0 | 0 | " |
| | 10 + 10 | 0 | 0 | 0 | 0 | 0 | 0 | 0 | 0 | 0 | " |
| | 15 + 20 | 0 | 0 | 0 | 0 | 0 | 0 | 0 | 0 | 0 | very slightly |
| Compound C + BCDA | 5 + 5 | 0.07 | 0 | 0.02 | 0.01 | 0.0 | 0.01 | 0.02 | 0.01 | 0.02 | nil |
| | 10 + 5 | 0.05 | 0 | 0 | 0 | 0 | 0 | 0 | 0 | 0 | " |
| | 10 + 10 | 0 | 0 | 0 | 0 | 0 | 0 | 0 | 0 | 0 | " |
| Compound D + BCDA | 5 + 5 | 0.07 | 0 | 0.01 | 0.01 | 0 | 0.02 | 0.01 | 0.02 | 0.02 | nil |
| | 10 + 5 | 0.04 | 0 | 0 | 0 | 0 | 0 | 0 | 0 | 0 | " |
| | 10 + 10 | 0 | 0 | 0 | 0 | 0 | 0 | 0 | 0 | 0 | " |
| MO Granular Agent-9 (commercially available product) | 27 | 0.01 | 0 | 0 | 0.07 | 0.97 | 0.08 | 2.01 | 4.02 | 0.07 | very slightly (browning of sheath) |
| Swep M Granular Agent (commercial product) | 60 + 2.1 | 0 | 0 | 0 | 0 | 0 | 0.01 | 0.01 | 0.09 | 0.04 | very severely (suppression of growth and occurrence of |

Table 1-continued

| Tested Compound or composition | Amount (g/a) | Annual Weeds | | | Perennial Weeds | | | | | | Chemical Damage on Rice plant |
|---|---|---|---|---|---|---|---|---|---|---|---|
| | | Echinochloa crusgalli | Cyperus difformis | Monochoria vaginalis presl | Scirpus hotarui | Eleocharis acicularis | Alisma canaliculatum a. br. et bouche | Sagittaria pygmaea miq. | Cyperus serotinus rottb | eleocharis kuroguwai ohwi | |
| Satan S Granular Agent (commercial Product) | 21 + 4.5 | 0 | 0 | 0 | 0.42 | 0.07 | 0.01 | 0.67 | 3.57 | 0.17 | rolling leaves Very severely (suppression of growth and withering of lower leaves) |
| Nil (blank test) | | 5.67 | 1.94 | 0.37 | 1.28 | 1.10 | 1.24 | 2.56 | 4.72 | 1.64 | nil |

TEST EXAMPLE 2

Herbicidal test in a growth stage in paddy field

A rice field soil in which various kinds of seeds and tubers of annual and perennial weeds were contained was introduced in a suitable amount into a pot having a size of 50 cm × 50 cm × 50 cm and made of concrete. To the soil was uniformly manured a chemical fertilizer to yield N, $P_2O_5$ and $K_2O$ components each in an amount of 3 g per pot. Then, water was irrigated in the pot. Four rice stubbles each composed of two rice plants of leaf stage of 2.5 were planted in the pot at equal intervals each other. 17 days after the plantation, a compound or composition to be tested which was prepared in almost the same manner as in the foregoing examples in the form of granules was applied to the pot under water-irrigated conditions.

One month after the application, a residual amount of the weeds and a chemical damage on the rice plants were checked. During the test, the filled water depth in the concrete pot was maintained at 3 cm and the filled water corresponding to 1 cm depth was continuedly allowed to leak over a period of 1 month.

The above tests were repeated using each component compounds or compositions of the invention and commercially available herbicidal products.

The test results are shown in Table 2 below.

Table 2

| Tested compound or composition | Amount (g/a) | Annual Weeds | | | Perennial Weeds | | | | | | | Rice plant | |
|---|---|---|---|---|---|---|---|---|---|---|---|---|---|
| | | Echinochloa crusgalli | Cyperus difformis | Monochoria vaginalis presl | Scirpus hotarui | Eleocharis acicularis | Sagittaria trifolia | Alisma canaliculatum a. br. et bouche | Sagittaria pygmaea miq. | Cyperus serotinus rottb | Eleocharis kuroguwai ohwi | Number of Halms (Halms/stubble) | Weight (air-dried weight g/stubble) |
| Compound A | 10.5 | 17.2 | 1.9 | 5.2 | 1.2 | 1.4 | 4.2 | 1.9 | 2.9 | 3.7 | 2.7 | 25 | 54.3 |
| | 21 | 15.7 | 1.2 | 4.1 | 0.9 | 0.9 | 2.7 | 1.0 | 2.1 | 1.9 | 1.7 | 26 | 56.9 |
| Compound B | 5.25 | 16.9 | 2.1 | 6.9 | 1.4 | 1.7 | 5.6 | 2.1 | 4.9 | 4.4 | 3.4 | 25 | 56.4 |
| | 10.5 | 16.4 | 1.3 | 4.2 | 1.1 | 1.1 | 2.1 | 1.2 | 2.7 | 3.9 | 1.9 | 26 | 56.8 |
| | 21 | 15.2 | 0.8 | 3.7 | 0.8 | 0.9 | 1.4 | 0.8 | 1.2 | 1.5 | 1.2 | 27 | 57.9 |
| Compound C | 10.5 | 16.8 | 1.7 | 4.8 | 1.2 | 1.3 | 3.9 | 1.4 | 3.2 | 3.4 | 2.4 | 26 | 56.1 |
| | 21 | 14.9 | 0.9 | 3.8 | 0.9 | 1.0 | 1.9 | 0.9 | 2.9 | 1.7 | 1.9 | 27 | 57.8 |
| Compound D | 10.5 | 16.7 | 1.8 | 5.7 | 1.3 | 1.6 | 4.0 | 1.5 | 3.0 | 3.7 | 2.4 | 27 | 56.0 |
| | 21 | 15.5 | 0.8 | 3.8 | 0.9 | 0.9 | 2.0 | 0.9 | 2.1 | 1.6 | 1.7 | 26 | 56.5 |
| BCDA | 3.75 | 3.9 | 2.7 | 8.4 | 2.1 | 0.8 | 6.4 | 2.7 | 4.9 | 4.1 | 2.4 | 28 | 58.6 |
| | 7.5 | 2.4 | 1.2 | 6.1 | 1.2 | 0.5 | 5.7 | 2.0 | 3.2 | 3.4 | 1.9 | 27 | 57.8 |
| | 15 | 0.4 | 0.8 | 1.0 | 1.1 | 0.4 | 5.2 | 1.9 | 2.9 | 1.9 | 1.2 | 25 | 56.4 |
| Compound A + BCDA | 10.5 + 3.75 | 0.4 | 0.2 | 0.5 | 0.3 | 0.1 | 0.1 | 0.1 | 0.2 | 0.5 | 0.2 | 28 | 58.2 |
| | 10.5 + 7.5 | 0 | 0 | 0 | 0 | 0 | 0.2 | 0.1 | 0 | 0.4 | 0.1 | 27 | 58.1 |
| | 21 + 3.75 | 0.6 | 0 | 0 | 0 | 0 | 0.1 | 0 | 0 | 0.2 | 0 | 29 | 58.6 |
| | 21 + 7.5 | 0.2 | 0.1 | 0 | 0 | 0 | 0 | 0 | 0 | 0.1 | 0 | 29 | 58.6 |
| | 21 + 15 | 0.1 | 0 | 0 | 0 | 0 | 0 | 0 | 0 | 0 | 0 | 28 | 58.4 |
| Compound B + BCDA | 5.25 + 3.75 | 0.9 | 0.2 | 0.4 | 0.2 | 0.1 | 0.2 | 0.1 | 0.2 | 0.4 | 0.4 | 28 | 58.6 |
| | 5.25 + 7.5 | 0 | 0 | 0 | 0 | 0 | 0 | 0 | 0 | 0 | 0 | 28 | 58.5 |
| | 5.25 + 15 | 0 | 0 | 0 | 0 | 0 | 0 | 0 | 0 | 0 | 0 | 27 | 58.1 |
| Compound C + BCDA | 10.5 + 3.75 | 0.6 | 0.4 | 0.6 | 0.1 | 0.2 | 0.1 | 0.1 | 0.1 | 0.1 | 0.2 | 28 | 58.4 |
| | 10.5 + 7.5 | 0 | 0 | 0 | 0 | 0 | 0 | 0 | 0 | 0 | 0 | 29 | 58.7 |
| | 21 + 3.75 | 0.5 | 0.6 | 0.4 | 0.2 | 0.1 | 0.1 | 0.1 | 0.2 | 0.5 | 0.2 | 28 | 58.9 |
| | 21 + 7.5 | 0 | 0 | 0 | 0 | 0 | 0 | 0 | 0 | 0 | 0 | 28 | 58.4 |
| Compound D + BCDA | 10.5 + 3.75 | 0.9 | 0.4 | 0.5 | 0.2 | 0.1 | 0.1 | 0.1 | 0.4 | 0.7 | 0.6 | 26 | 58.2 |
| | 10.5 + 7.5 | 0 | 0.1 | 0 | 0.1 | 0 | 0.1 | 0.1 | 0.1 | 0.2 | 0.1 | 27 | 58.0 |
| | 21 + 7.5 | 0 | 0.1 | 0 | 0 | 0 | 0 | 0 | 0 | 0 | 0 | 28 | 57.9 |
| MO granular agent-9 (commercially available product) | 27 | 12.4 | 3.2 | 9.2 | 2.4 | 1.9 | 6.4 | 1.7 | 4.9 | 5.1 | 1.9 | 21 | 42.8 |
| Swep M granular agent (commerci- | | | | | | | | | | | | | |

Table 2-continued

| Tested compound or composition | Amount (g/a) | Annual Weeds | | | Perennial Weeds | | | | | | | Rice plant | |
|---|---|---|---|---|---|---|---|---|---|---|---|---|---|
| | | Echinochloa crusgalli | Cyperus difformis | Monochoria vaginalis presl | Scirpus hotarui | Eleocharis acicularis | Sagittaria trifolia | Alisma canaliculatum a. br. et bouche | Sagittaria pygmaea miq. | Cyperus serotinus rottb | Eleocharis kuroguwai ohwi | Number of Halms (Halms/ stubble) | Weight (airdried weight g/stubble) |
| ally available product) Satan S granular agent | 60 + 2.1 | 1.3 | 0.6 | 1.1 | 0.4 | 0.3 | 1.4 | 0.2 | 1.2 | 1.4 | 1.1 | 24 | 56.8 |
| (commercially available product) | 21 + 4.5 | 1.0 | 0.4 | 1.3 | 1.7 | 0.2 | 4.2 | 0.9 | 4.7 | 2.1 | 2.9 | 25 | 54.9 |
| Non-treated and let-alone pot | — | 15.6 | 4.7 | 12.1 | 2.9 | 2.4 | 7.1 | 2.1 | 5.6 | 4.9 | 3.2 | 18 | 40.1 |
| Non-treated but hand-weeded pot | — | — | — | — | — | — | — | — | — | — | — | 29 | 58.5 |

TEST EXAMPLE 3

Herbicidal field test in paddy field

A rice field which was naturally overgrown with various kinds of usual paddyfield weeds was cultivated, manured (with N,P$_2$O$_5$ and K$_2$O each in an amount of 1 kg/are), raked and prepared, being partitioned into a number of sections each having an area of 10 m$^2$ (2.5 m×4 m). Then, rice stubbles each of which was composed of two paddyfield young rice plants having a leaf stage of 2.5 were tranplanted at levee and stubble distances of 30 cm and 15 cm, respectively. After transplantating the depth water was maintained at 3-5 cm. Then, various kinds of compounds or compositions of the invention which were prepared in the same manner as described in the foregoing examples in the form of granules were scattered by hand on the field in an initial stage of germination of weeds (3 days after the transplanation) and in a leaf stage of 3.0-3.5 (15 days after the transplanation).

For comparison, commercially available MO granular 9 and Satan-s granular were also tested in the same method as illustrated hereinabove. The residual amount of weeds and yields of rice were determined one month after the application and four months thereafter, respectively.

The test results are shown in Table 3.

Table 3

| Tested Compound, or composition | Amount (g/a) | Treatment after 3 days after transplantation | | | | | | Yield of Rice plant (kg/a) |
|---|---|---|---|---|---|---|---|---|
| | | Orizycola | Other weeds | | | | | |
| | | | Annual | | Perennial | | | |
| | | | Cyperus difformis | Broadleaved weeds | Scirpus juncoides | Sagittaria pygmaea miq. | Sagittaria trifolias. | |
| Compound A (7%*) | 10.5 | 29.8 | 1.9 | 2.9 | 1.4 | 2.7 | 4.2 | 40.7 |
| | 21 | 27.9 | 1.4 | 1.5 | 1.1 | 1.5 | 2.1 | 41.6 |
| Compound B (10%*) | 15 | 29.4 | 1.5 | 2.7 | 1.8 | 1.9 | 2.8 | 41.9 |
| | 30 | 28.2 | 1.1 | 1.2 | 0.9 | 1.2 | 1.9 | 42.3 |
| Compound C (10%*) | 15 | 29.6 | 1.7 | 2.9 | 1.9 | 2.1 | 2.9 | 41.4 |
| | 30 | 28.5 | 1.2 | 1.5 | 1.2 | 1.6 | 2.1 | 42.7 |
| Compound D (10%*) | 15 | 29.5 | 1.9 | 2.9 | 1.6 | 2.2 | 3.5 | 41.9 |
| | 30 | 28.1 | 1.3 | 1.4 | 1.0 | 1.7 | 2.1 | 41.7 |
| BCDA | 7.5 | 2.9 | 1.2 | 2.6 | 1.6 | 6.9 | 7.2 | 47.8 |
| | 15 | 1.6 | 0.9 | 1.4 | 1.1 | 4.5 | 2.8 | 46.7 |
| Compound A + BCDA (7% + 5%*) | 10.5 + 7.5 | 0.6 | 0.3 | 0.2 | 0.4 | 0.2 | 0.1 | 48.9 |
| | 21 + 15 | 0 | 0 | 0 | 0 | 0 | 0 | 49.2 |
| Compound B + BCDA (10%*) | 15 + 7.5 | 0.2 | 0.1 | 0.1 | 0.2 | 0.1 | 0.4 | 48.7 |
| | 30 + 15 | 0 | 0 | 0 | 0 | 0 | 0 | 48.6 |
| Compound C + BCDA (10%*) | 15 + 7.5 | 0.4 | 0.4 | 0.2 | 0.3 | 0.2 | 0.3 | 49.1 |
| | 30 + 15 | 0 | 0 | 0 | 0 | 0 | 0 | 49.2 |
| Compound D + BCDA (10% + 5%*) | 15 + 7.5 | 0.3 | 0.2 | 0.2 | 0.3 | 0.1 | 0.3 | 49.0 |
| | 30 + 15 | 0 | 0 | 0 | 0 | 0 | 0 | 49.1 |
| MO Granular Agent-9 (commercial product) | 27 | 2.7 | 0.7 | 0.7 | 4.9 | 13.1 | 11.4 | 49.2 |
| Satan S granular agent (commercial | 21 + 4.5 | 0.7 | 0.2 | 0.1 | 2.8 | 10.7 | 6.7 | 36.7 |

Table 3-continued

| | | | | | | | |
|---|---|---|---|---|---|---|---|
| product) Non-treated and let-alone area | | 28.7 | 6.9 | 7.4 | 6.4 | 12.1 | 10.7 | 37.4 |
| Non-treated but hand-weeded area | | — | — | — | — | — | — | 48.6 |

| | | Treatment after 15 days after transplantation | | | | | |
|---|---|---|---|---|---|---|---|
| | | | Other weeds | | | | Yield |
| | | | Annual | | Perennial | | of |
| Tested Compound, or composition | Amount (g/a) | Orizy-cola | Cyperus difformis | Broad-leaved weeds | Scirpus juncoides | Sagittaria pygmaea miq. | Sagittaria trifolias | Rice plant (kg/a) |
| Compound A (7%*) | 10.5 | 31.4 | 2.9 | 7.2 | 4.9 | 7.2 | 4.9 | 38.6 |
| | 21 | 30.8 | 1.4 | 2.9 | 2.1 | 1.8 | 2.5 | 39.6 |
| Compound B (10%*) | 15 | 30.9 | 2.7 | 3.4 | 3.1 | 2.7 | 3.9 | 39.5 |
| | 30 | 29.4 | 1.8 | 1.7 | 1.9 | 1.2 | 1.8 | 40.7 |
| Compound C (10%*) | 15 | 31.9 | 2.9 | 4.2 | 3.5 | 2.9 | 4.2 | 40.2 |
| | 30 | 28.7 | 1.9 | 1.9 | 2.1 | 1.7 | 2.6 | 41.7 |
| Compound D (10%*) | 15 | 31.0 | 2.9 | 5.4 | 3.3 | 2.8 | 4.0 | 39.9 |
| | 30 | 29.5 | 1.8 | 1.9 | 2.1 | 1.6 | 2.4 | 40.1 |
| BCDA | 7.5 | 4.7 | 3.7 | 5.6 | 3.8 | 5.8 | 5.8 | 46.5 |
| | 15 | 2.9 | 1.9 | 2.7 | 1.8 | 3.7 | 2.2 | 47.4 |
| Compound A + BCDA (7% + 5%*) | 10.5 + 7.5 | 0.9 | 0.4 | 0.7 | 0.7 | 0.6 | 0.5 | 48.3 |
| | 21 + 15 | 0.4 | 0.2 | 0.2 | 0.2 | 0.4 | 0.5 | 48.6 |
| Compound B + BCDA (10%*) | 15 + 7.5 | 0.6 | 0.6 | 0.4 | 0.1 | 0.1 | 0.2 | 48.5 |
| | 30 + 15 | 0.2 | 0 | 0 | 0 | 0 | 0 | 48.7 |
| Compound C + BCDA (10%*) | 15 + 7.5 | 0.7 | 0.9 | 0.6 | 0.1 | 0.2 | 0.2 | 48.6 |
| | 30 + 15 | 0.3 | 0 | 0 | 0 | 0 | 0 | 49.1 |
| Compound D + BCDA (10% + 5%*) | 15 + 7.5 | 0.6 | 0.8 | 0.6 | 0.1 | 0.1 | 0.2 | 49.0 |
| | 30 + 15 | 0.4 | 0 | 0 | 0 | 0 | 0 | 48.7 |
| MO Granular Agent-9 (commercial product) | 27 | 24.5 | 5.8 | 4.5 | 5.7 | 8.4 | 9.7 | 42.7 |
| Satan S granular agent (commercial product) | 21 + 4.5 | 4.1 | 1.7 | 1.8 | 1.4 | 12.7 | 10.9 | 48.6 |
| Non-treated and let-alone area | | 30.4 | 7.8 | 8.2 | 7.9 | 14.2 | 11.7 | 37.4 |
| Non-treated but hand-weeded area | | — | — | — | — | — | — | 48.6 |

*granular agent

TEST EXAMPLE 4

Herbicidal test in upland/field 3.5 kg of an air-dried fine field soil (capable of passing a 14 mesh per inch screen) was placed in an 1/5000 are pot and uniformly manured with a chemical fertilizer which contained N, $P_2O_5$ and $K_2O$ components each in an amount of 0.5 kg. Then, the soil moisture was adjusted to 60% of a maximum water contents in the soil. A predetermined amount of seeds of a crop and weeds to be tested was sowed and uniformly covered with the soil. Thereafter, the wettable powder prepared in accordance with the foregoing examples using a certain amount of component compound or composition of the invention were applied to the soil, respectively, and the pots treated were placed in a green house to allow the seeds to grow.

30 days after the sowing, the germination and growth of the crop and weeds were observed to obtain the results of Table 4.

In the Table, the degree of chemical damage on the crop and the herbicidal effect on the weeds are expressed in terms of five-grades-estimation wherein grade "0" intends to mean such degrees of germination or growth of the crop or weeds as those in a non-treated, while grade "5" means the complete suppression of growth of the weeds, five grades being provided between grades "0" and "5".

Table 4

| Tested compound or composition | Amount of effective component (g/a) | Herbicidal effect on weeds | | | | | | | | | |
|---|---|---|---|---|---|---|---|---|---|---|---|
| | | Rice plant | Corn | Soy-bean | Wheat | Digitaria adscendens | Alopecurus aequalis sobol | Poa annua | Chenopodium album | Amaranthus retroflexus | stellaria media villars |
| Compound A | 10 | 0 | 0 | 0 | 0 | 0 | 0 | 0 | 0 | 0 | 0 |

Table 4-continued

| Tested compound or composition | Amount of effective component (g/a) | Rice plant | Corn | Soy-bean | Wheat | Digitaria adscendens | Alopecurus aequalis sobol | Poa annua 1 | Chenopodium album 1 | Amaranthus retroflexus 1 | stellaria media villars |
| --- | --- | --- | --- | --- | --- | --- | --- | --- | --- | --- | --- |
|  | 20 | 0 | 0 | 0 | 0 | 0 | 0 | 0 | 0 | 0 | 0 |
|  | 30 | 0 | 0 | 0 | 0 | 0 | 1 | 0 | 1 | 1 | 1 |
| Compound D | 10 | 0 | 0 | 0 | 0 | 0 | 0 | 0 | 0 | 0 | 0 |
|  | 20 | 0 | 0 | 0 | 0 | 0 | 0 | 0 | 0 | 0 | 0 |
|  | 30 | 0 | 0 | 0 | 0 | 0 | 0 | 0 | 0 | 0 | 0 |
| BCDA | 5 | 0 | 0 | 0 | 0 | 0 | 0 | 0 | 0 | 0 | 0 |
|  | 10 | 0 | 0 | 0 | 0 | 1 | 1 | 1 | 0 | 0 | 0 |
|  | 20 | 1 | 1 | 0 | 1 | 2 | 2 | 2 | 1 | 1 | 1 |
| Compound A + | 10 + 5 | 0 | 0 | 0 | 0 | 4–5 | 4–5 | 4–5 | 4–5 | 4–5 | 4–5 |
|  | 10 + 10 | 0 | 0 | 0 | 0 | 5 | 5 | 5 | 5 | 5 | 5 |
| BCDA | 20 + 5 | 0 | 0 | 0 | 0 | 5 | 5 | 5 | 5 | 5 | 5 |
|  | 20 + 10 | 0 | 0 | 0 | 0 | 5 | 5 | 5 | 5 | 5 | 5 |
|  | 30 + 10 | 1 | 1 | 1 | 1 | 5 | 5 | 5 | 5 | 5 | 5 |
| Compound D + | 10 + 5 | 0 | 0 | 0 | 0 | 4–5 | 4–5 | 4–5 | 4–5 | 4–5 | 4–5 |
|  | 10 + 10 | 0 | 0 | 0 | 0 | 5 | 5 | 5 | 5 | 5 | 5 |
| BCDA | 20 + 5 | 0 | 0 | 0 | 0 | 5 | 5 | 5 | 5 | 5 | 5 |
|  | 20 + 10 | 0 | 0 | 0 | 0 | 5 | 5 | 5 | 5 | 5 | 5 |
|  | 30 + 20 | 1 | 1 | 1 | 1 | 5 | 5 | 5 | 5 | 5 | 5 |

As will be clear from the above results, the use of the herbicidal compositions of the present invention in the paddy-field gives no ill effect on rice plants even when the composition is applied in any stage from the initial germination of weeds or immediately after the planting of the plant rice plant to the height of growth of the weeds. Further, the composition of the invention serves to control all of the weeds in only one spraying, thus being much more excellent over known herbicides.

In addition, the herbicidal compositions of the invention are also utilizable in upland fields, exhibit excellent herbicidal characteristics, and are applicable to various kinds of weeds over a long period of application time. As in the case of the paddyfield, they are very useful as a herbicide for application to crops.

What is claimed is:

1. A herbicidal composition comprising as active ingredients herbicidally effective amounts of at least one α-(β-naphthoxy)propionic acid derivative expressed by the formula:

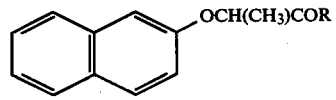

wherein R represents OH, OCH₃,

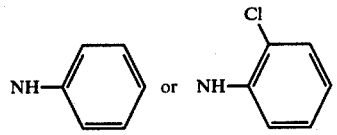

and N-(butoxymethyl)-2-chloro-2',6'-diethyl acetanilide, the ratio of N-(butoxymethyl)-2-chloro-2',6'-diethyl acetanilide to α-(β-naphthoxy)propionic acid derivative being about 0.179–2.8:1 by weight, said composition being herbicidally effective against both perennial weeds and annual weeds at applications of 10–40 g/are based on the total weight of said active ingredients.

2. A herbicidal composition according to claim 1, wherein the total amount of the said active ingredients ranges from 10 to 70% by weight.

3. A herbicidal composition according to claim 1, wherein said composition is in the form of granular, wettable powder, or dust.

4. A herbicidal composition according to claim 3, wherein said granular contains therein 10–20% of said active ingredients.

5. A herbicidal composition according to claim 3, wherein said wettable powder contains therein 60–70% of said active ingredients.

6. A herbicidal composition according to claim 1, further comprising a diluent, filler or adjuvant.

7. A herbicidal composition according to claim 6, wherein said adjuvant is a stabilizing agent, dispersing agent, a suspending agent, a spreader, a penetrating agent or a wet spreader.

8. A herbicidal composition according to claim 1, further comprising a fungicide, an insecticide, agricultural chemicals or a soil conditioner.

9. A method for controlling both annual weeds and perennial weeds which comprises applying herbicidally effective amounts of at least one α-(β-naphthoxy) propionic acid derivative expressed by the formula:

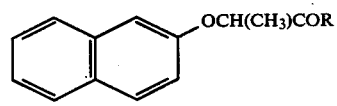

wherein R represents OH, OCH₃,

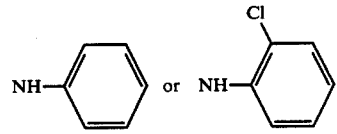

and N-(butoxymethyl)-2-chloro-2',6'-diethyl acetanilide to the weeds in amounts of 5.25–30 g/are and 3.75–20 g/are, respectively, the ratio of N-(butoxymethyl)-2-chloro-2', 6'-diethyl acetanilide to α-(β-naphthoxy)propionic acid derivative being about 0.179–2.8:1 by weight, and wherein the total amount of said propionic acid derivative and said acetanilide is applied within the range of 10–40 g/are.

10. A method for controlling both annual weeds and perennial weeds according to claim 9 wherein said α-(β-naphthoxy)propionic acid derivative and said N-(butoxymethyl)-2-chloro-2',6'-diethyl acetanilide are applied in amounts of 10.5–30 g/are and 7.5–15 g/are respectively, the ratio of N-(butoxymethyl)-2-chloro-2',6'-diethyl acetanilide to α-(β-naphthoxy)propionic acid derivative being about 0.179–2.8:1 by weight, and wherein the total amount of said propionic acid derivative and said acetanilide is applied within the range of 10–40 g/are.

11. A method for controlling both, annual weeds and perennial weeds according to claim 9 wherein said α-(β-naphthoxy)propionic acid derivative and said N-(butoxymethyl)-2-chloro-2',6'-diethyl acetanilide are applied in amounts of 10–30 g/are and 5–20 g/are, respectively, the ratio of N-(butoxymethyl)-2-chloro-2',6'-diethyl acetanilide to α-(β-naphthoxy)propionic acid derivative being about 0.179–2.8:1 by weight, and wherein the total amount of said propionic acid derivative and said acetanilide is applied within the range of 10–40 g/are.

12. A method for controlling weeds according to claim 9 wherein the ratio of N-(butoxymethyl)-2-chloro-2',6' diethyl acetanilide to α-(β-naphthoxy) propionic acid derivative is 0.3–1:1 by weight.

13. A herbicidal composition according to claim 1, wherein the ratio of N-butoxymethyl-2-chloro-2',6'-diethyl acetanilide to α-(β-naphthoxy) propionic acid derivative is 0.3–1:1 by weight.

* * * * *